United States Patent [19]
Guice

[11] Patent Number: 5,355,684
[45] Date of Patent: Oct. 18, 1994

[54] CRYOGENIC SHIPMENT OR STORAGE SYSTEM FOR BIOLOGICAL MATERIALS

[76] Inventor: Walter L. Guice, 19640 FM 1804, Lindale, Tex. 75771

[21] Appl. No.: 876,406

[22] Filed: Apr. 30, 1992

[51] Int. Cl.⁵ .............................................. F17C 7/00
[52] U.S. Cl. ........................................ 62/54.2; 62/60; 62/457.2; 62/457.9
[58] Field of Search ............... 62/59, 60, 54.2, 54.1, 62/457.9, 457.2, 434, 45.1

[56] References Cited

U.S. PATENT DOCUMENTS

| | | | |
|---|---|---|---|
| 3,406,531 | 10/1968 | Swenson et al. | 435/1 X |
| 3,745,785 | 7/1973 | Crawford et al. | 62/60 |
| 3,810,367 | 5/1974 | Peterson | 62/457 |
| 3,864,927 | 2/1975 | Li | 62/54.3 |
| 3,864,935 | 2/1975 | Elson | 62/60 |
| 4,262,494 | 4/1981 | Karow | 62/384 |
| 4,292,817 | 10/1981 | Loucks | 62/457 |
| 4,473,637 | 9/1984 | Guilbert | 435/1 |
| 4,502,295 | 5/1985 | Toledo-Pereyra | 62/463 |
| 4,530,816 | 7/1985 | Douglas-Hamilton | 62/463 |
| 4,576,017 | 3/1986 | Combs et al. | 62/372 |
| 4,597,266 | 7/1986 | Entrekin | 62/54.3 |
| 4,723,974 | 2/1988 | Ammerman | 62/4 |
| 4,862,674 | 9/1989 | Lejondahl et al. | 53/432 |
| 4,903,493 | 2/1990 | Van Iperen et al. | 62/60 |
| 4,947,658 | 8/1990 | Wheeler et al. | 62/372 |
| 4,951,482 | 8/1990 | Gilbert | 62/457.1 |
| 4,955,480 | 9/1990 | Sexton | 62/371 |
| 4,958,506 | 9/1990 | Guilhem et al. | 62/457 |

Primary Examiner—Ronald C. Capossela

[57] ABSTRACT

A system for the storage or shipment of frozen or chilled biological materials consisting of a cryogenically insulated vessel which contains a heat sink material. The heat sink material is initially chilled to a very low temperature to keep the contents of the vessel cold. The heat sink may include a change of phase to provide extension of the possible shipment or storage time at a relatively constant temperature.

17 Claims, 5 Drawing Sheets

CRYOGENIC SHIPMENT OR STORAGE SYSTEM FOR BIOLOGICAL MATERIALS

BACKGROUND

1. Field of Invention

This invention relates to a system to be used for the shipment or temporary storage of frozen or chilled biological materials such as semen, blood, embryos, bone marrow, and organs.

BACKGROUND: CURRENT STATE OF THE ART

2. Introduction: Cryogenic vs. Noncryogenic Systems

Cryogenics is defined as the science which deals with extremely low temperatures. In general, the science which deals with ordinary freezing of foodstuffs or cold weather is noncryogenic, since this science deals in temperatures experienced by humanity in the normal or expected environment. That science dealing with liquefied or frozen gases and/or the temperatures at which such liquefaction or freezing occurs while at a pressure near normal atmospheric pressure is properly cryogenics.

Artificial insemination of animals; transfer of preserved embryos; blood transfusions; and transplant of organs, bone marrow, or corneas all require the use of biological materials which frequently must be shipped from the point of production to the final point at which they are to be used while at a temperature in the cryogenic range. This creates certain handling difficulties which can be better addressed by better technology.

3. Prior Art: Noncryogenic Systems

U.S. Pat. No. 4,947,658, by Wheeler, et. al., teaches the use of a vessel filled with a frozen substance and a nonfrozen substance, which frozen substance is used to keep the nonfrozen substance cool, as well as act as a heat sink to help keep frozen a second frozen substance. The vessel consists of an insulated chest with four walls a bottom and an open top with a space for a refrigerant material below a shelf support. The shelf support supports an insulated shelf which shelf is used to control the heat transfer between the frozen refrigerant and the unfrozen material which is stored on the shelf. The shelf is of course removable to allow access to the refrigerant material and the frozen substances shipped with it. It is intended for ordinary cold, as opposed to cryogenic, temperatures.

U.S. Pat. No. 4,576,017, issued to Combs, et. al. (1986), teaches the use of an insulated vessel containing a heat exchange medium used in conjunction with an open space to allow convection currents to keep a frozen material at a substantially constant temperature. The system does not utilize a heat sink or other thermal storage means, thus the retention time at a given temperature is limited by the thermal mass of the stored material and by the efficiency of the insulation. Sexton, in U.S. Pat. No. 4,955,480, (1990) teaches the use of a box made of expanded polystyrene foam containing a plastic container which holds a frozen liquid, which frozen liquid is in turn hollow and in which pharmaceutical solutions are placed for shipment. The polystyrene foam, with an average thermal conductivity in the range of 0.033 Watts/meter degree K., (compared to a Dewar flask with an effective conductivity about 100 times lower) is not very effective as a cryogenic insulator, but the Sexton invention is concerned with shipment of materials in the range of 0 to 4 degrees C. Ammerman, in U.S. Pat. No. 4,723,974, (1988) teaches of a flexible double wall container, between the walls of which is placed a pair of separately packaged materials which cool when their packages are ruptured and they are allowed to mix. The inner container is meant to be used for shipping amputated extremities.

U.S. Pat. No. 4,502,295, issued to Toledo-Pereyra, (1985) teaches the use of a container made of plastic, having a plurality of receptacles and containing an inner container filled with ice in a manner similar to the previously cited method of Wheeler et. al. and having a drain to allow melted icewater to run out. The container must be kept vertical so that the water can drain out as the ice melts, thus maintaining a uniform internal temperature. The receptacles are intended for constant-temperature shipment of organs at a temperature between 0 degrees and 7 degrees C. during shipment. U.S. Pat. No. 4,951,482, by Gilbert (1990), uses a double walled container for shipping organs. A means is included for circulating an externally chilled refrigeration fluid between the walls. Swenson and Koski, in U.S. Pat. No. 3,406,531, (1968) use a similar system in which organs are kept at a constant temperature between 0 degrees and 4 degrees C. by circulating a refrigerant liquid between the container and a refrigerant system. An external refrigerator system is required for this system. Peterson, in U.S. Pat. No. 3,810,367, (1974) illustrates the use of a double walled insulated vessel with a mixture of ice and water between the walls, to ship human organs at a constant 32 degree F. temperature.

Douglas-Hamilton, in U.S. Pat. No. 4,530,816, (1988) teaches the use of ice in an insulated vessel, which ice is separated from a biological material by a sheet of insulating material, similar in manner to the previously cited methods of Wheeler et. al. and of Toledo-Pereyra. The insulating layer is used to maintain the chilled specimen in a temperature range just above freezing for storage and/or transport. The thickness of the insulating layer between the ice and the stored material is selected so as to impart an optimum heat extraction rate to the specimen in order to result in a steady-state temperature just above freezing for shipment. This cooling control and above-zero storage is necessary to optimize the postthaw motility rate in the case of equine semen. Vertical orientation is required during shipment and storage to keep the ice on the bottom.

Guilhem and Wengler, U.S. Pat. No. 4,958,506 (1990) (French appln. no. 88 02845), teach of an insulated container having two compartments, a lower one filled with a mixture of ice and water, and an upper one filled with water and a biological component such as an organ to be transplanted. A heat transfer means such as a heat pipe is used to transfer heat from the upper to the lower compartment so as to maintain the temperature just above freezing during transportation.

All the immediately preceding nine patents are intended for storage and/or shipment at temperatures below the normal ambient, but well above the cryogenic (below zero Celsius) temperatures required for storage and shipment of bovine semen and embryos and human blood.

Loucks, in U.S. Pat. No. 4,292,817 (1981), teaches the use of an insulated container holding liquid filled members for conductive heat transfer between a temperature control means and the interior of the vessel. This method requires the use of an external refrigeration means. Guilbert, in U.S. Pat. No. 4,473,637, (1984) teaches of an insulated shipping box containing a powered refrigeration unit for the purpose of shipping organs. Both of these inventions could be adapted for cryogenic use, but both have the disadvantage of requiring an externally powered refrigeration unit attached to or in conjunction with the storage device.

4. Prior Art: Cryogenic Systems

In the early days of artificial insemination, it was discovered that semen of many animals could be kept almost indefinitely by freezing it in dry ice at about minus 80 degrees C. More recently it has been discovered that fertilized ova, blood, eye corneas, and bone marrow can be similarly preserved. However, dry ice is a dangerous substance to ship, since it releases carbon dioxide as it melts, which can displace oxygen in a shipping vehicle and cause asphyxiation. Also, a long shipment could require frequent replenishment of the dry ice. Thus the current system of shipping in liquid nitrogen was born.

The current state of the art of cryogenic shipping or storage of semen normally involves the use of Dewar flask vessels such as those manufactured by Minnesota Valley Engineering. These vessels are filled with liquified nitrogen at around minus 196 degrees C. in which the semen is immersed. The liquid nitrogen acts as a heat sink, changing from liquid to gas as the interior of the vessel gains heat. This liquid-to-gas phase change inherent in the liquid nitrogen shipping concept requires that the tanks must be continuously vented, so that a pressure buildup due to gas does not rupture the tank. The semen is stored in straws which are suspended in cannisters via rods into the nitrogen.

The flasks consist of an inner aluminum vessel and an outer vessel which is normally made of stainless steel. The aluminum inner vessel is suspended from the neck of the outer vessel by an extended neck normally made of a fiberglass epoxy resin, which design is used to minimize heat conduction out of the flask through the neck. The space between the inner and outer vessel is evacuated or filled with a superinsulation material to minimize heat transfer between the two. A well-designed flask of this design is capable of storing a load of biological materials for up to six months on a single filling of liquid nitrogen.

The flasks weigh from a minimum of around 25 pounds up to around 135 pounds, and must be shipped in the upright position, to avoid spillage of nitrogen from the tanks and/or spilling the semen straws into the nitrogen. A variation on this system, also manufactured by Minnesota Valley Engineering, uses an absorbent material as an inner tank liner. The lining absorbs liquid nitrogen which is poured in to act as a heat sink, thus this system avoids the spillage problems. The liquid nitrogen is constantly boiled off as a result of heat transfer into the tank, thus if the container is placed in an enclosed space the ambient air can become too nitrogen-rich, leading to a potential of asphyxiation. Most commercial shippers cannot accept such a load due to legal or safety considerations, so the nitrogen tanks are normally shipped by bus. Even if only a single 1 cc straw of semen is to be shipped, the 25 pound minimum container is required. The same techniques are used for the shipment of frozen embryos to be used in embryo transfers. Occasionally chilled organs are shipped on "dry ice" (frozen $CO_2$) in an ice chest, but the hazardous nature of the $CO_2$ gas that is necessarily created as a result of warming makes this a very expensive process.

U.S. Pat. No. 4,862,674, issued to Lejondahl et. al. (1989), features a double walled shipping container with a multi-layer composite superinsulation material between the walls. An inner container is to be filled with a vaccine or other biological material as well as a solid-to-liquid phase change material which acts as a heat sink. After being loaded, the inner container is hermetically sealed and wrapped with the insulating material, then placed inside the outer container. The outer container is then hermetically sealed and the space between the two containers is evacuated with a vacuum pump. Due to the requirement to evacuate the containers each time they are used, the system is intended to be used for one time use only. Creation of a hard vacuum each time the system is used is a severe disadvantage, but the system is efficient enough to allow up to six months of relatively constant low temperature storage.

Karow, in U.S. Pat. No. 4,262,494, (1981) teaches the use of an insulated double walled container to be used for freezing semen and similar biological materials at a controlled rate as well as for shipment of such materials. The freezing and temperature retention are accomplished by placing in the container a quantity of a solid-to-gas phase change material such as frozen $CO_2$, which must be vented to the outside of the container. Such venting creates a potential safety problem when placed in an enclosed space.

Both the Lejondahl et. al. invention and the Karow invention, as well as the previously cited liquid nitrogen tanks, could be effectively used for the storage of frozen semen and/or embryos. However the liquid nitrogen system and the Karow system both depend upon the a phase change which results in production of a potentially harmful gas, and both must be vented to allow the gas to escape. The Lejondahl et. al. system avoids this problem by use of a solid-to-liquid phase change, but requires wrapping the inner container with insulation and creation of a hard vacuum in the system whenever it is packed.

SUMMARY OF THE CURRENT INVENTION

The current invention involves a comparably lightweight and safe shipping system to replace the prior art. This system shall be passive, in that no external heat extraction means shall be used to maintain the low temperature. A shipment of chilled or frozen biological materials is fitted into a cryogenically insulated vessel such as a Dewar flask or a vessel having an evacuated multi-layer superinsulation material or an evacuated powder insulation material. The shipment is kept cold by means of one or more heat sinks which are initially chilled to the temperature of a liquified gas (about minus 196 degrees C., in the case of nitrogen) and then placed in the cryogenically insulated vessel with the biological materials. Alternatively, the heat sink material can be placed in the vessel and cooled in place, either by flooding the interior of the tank with a suitable liquified gas (such as liquid nitrogen) or by the use of an insertable heat exchanger attached to an external refrigeration unit. In the preferred embodiment, the heat sink material shall be made of a substance which changes phase at or slightly below the maximum permissible preservation temperature of the materials, to be shipped, as described below. This heat sink material would in the preferred embodiment be composed of a mixture of water and a low temperature freezing material such as ethylene glycol or alcohol, and would remain in a liquid state at the maximum temperature to which the shipping system would be exposed.

A phase change is a very effective means of creating a constant temperature heat sink, as taught by Lejondahl et. al. (U.S. Pat. No. 4,862,674), Sexton (U.S. Pat. No. 4,955,480), Toledo-Pereyra (U.S. Pat. No. 4,502,295), Karow (U.S. Pat. No. 4,262,494), and Douglas-Hamilton (U.S. Pat. No. 4,530,816). An example is the case of ice changing to liquid water at a constant temperature of 32 degrees F. while absorbing about 143.3 BTU/lb. in the process. The use of the heat sink permits constant temperature absorption of the heat which enters the system as a result of inefficiencies in the insulation system.

In the preferred embodiment, the cryogenically insulated vessel of the current invention shall be placed in an outer shipping container which is lined with a secondary insulating layer. The cryogenically insulated vessel may be permanent placed in the outer shipping vessel or it may be removable. The secondary insulating layer between the inner and outer containers, which preferably would be made of a foam such as polyethylene or polystyrene, would serve to protect against mechanical damage. It would have a secondary use as additional thermal insulation.

The current invention requires the use of a conventional nitrogen tank or other cryogenic refrigeration means at the location from which the shipment is to be sent. The requirement for an external refrigeration means in permanent use with the shipment, as in the cases of Loucks (U.S. Pat. No. 4,292,817), Gilbert (U.S. Pat. No. 4,951,482) and Koski and Swenson (U.S. Pat. No. 3,406,531) is thus avoided. Since there is no significant volume change in the solid-to-liquid or solid-to-solid phase change, the system can be shipped completely sealed. Since the current invention can be sealed, it is capable of being shipped in any orientation. This avoids the vertically upright restrictions of the liquid nitrogen tanks, the Guilhem and Wengler system (U.S. Pat. No. 4,958,506), the Toledo-Pereyra system (U.S. Pat. No. 4,502,295) and the Douglas-Hamilton system (U.S. Pat. No. 4,530,816) system. The current invention also avoids the danger of the dry ice as shown in the Karow system (U.S. Pat. No. 4,262,494) and the use of one-time-only chemical reaction coolants as in the Ammerman system (U.S. Pat. No. 4,723,974). Since the insulation is accomplished by permanent means in the current invention, there is no need to reestablish the vacuum when the system is packed, as there is in the Lejondahl et. al. (U.S. Pat. No. 4,862,674) system.

The use of a true cryogenic insulation system in the current invention permits much colder temperatures to be achieved and maintained than in the Sexton (U.S. Pat. No. 4,955,480) system. Since semen can be effectively stored at any temperature between absolute zero and about minus 80 degrees C., and blood can be stored at any temperature between absolute zero and about minus 40 degrees C., storage at a fixed temperature is not required. Thus the heat sink material can be cooled to a relatively low temperature as compared to all the previously cited references except possibly the Karow (U.S. Pat. No. 4,262,974) system.

DESCRIPTION OF DRAWINGS AND FIGURES

DETAILED DESCRIPTION OF THE INVENTION

Description of the Heat Sink Material

Figure 1:
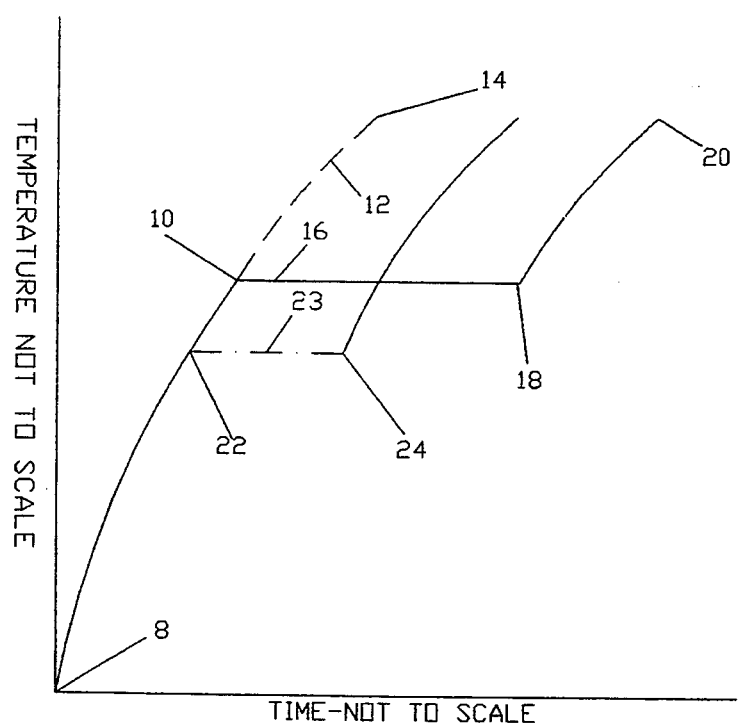
FIG. 1 shows a graphic illustration of the temperature vs. time behavior of heat sinks both with and without phase changes.

The current invention uses a heat sink material which is selected for its ability to absorb a large quantity of heat in a small amount of volume and/or mass. This material should preferrably have as high as possible a value of net specific heat multiplied by density. A cryogenically insulated reusable and resealable vessel is used to hold both the biological materials and the heat sink(s). In the preferred embodiment, the heat sink(s) shall be located in such a fashion as to at least partially surround the biological materials, similar to the method taught by Sexton (U.S. Pat. No. 4,955,480).

Specific heat is the amount of heat a substance absorbs or emits for a given change in temperature; density is its weight per unit volume. Net specific heat includes both sensible heat (energy potential which results in a change of temperature) and latent heat (energy potential which results in a change of phase or of state.) Thus the product of net specific heat and density is a measure of energy absorption capacity per unit temperature change per unit volume.

The heat sink(s) could be made of a material which remains in a single solid phase throughout the temperature range in which the material is to be stored, which range might be for example between the temperature of liquid nitrogen and that of dry ice. In this case all the heat capacity of the heat sink material would be in sensible heat.

In the preferred embodiment, the heat sink(s) should be made of a substance which changes phase at a selected temperature or temperature range, and absorbs energy as a result of the phase change. This phase: change could be either from a solid to a liquid phase, or it could be from a solid to a second solid phase. This phase change material could be made to hold the entire shipment at a relatively constant and selected given temperature for an extended time span as the material changes phase, as in the case of ice changing to liquid water at a fixed temperature of about 0 degrees C. The heat sink could be composed of bars of a size to permit their being immersed for cooling in a conventional nitrogen tank such as those used for storage of semen, by placing such bars in the canisters previously mentioned. Alternately the heat sink could be placed directly inside the cryogenically insulated vessel and cooled in place.

The heat sink could be made of a mixture of substances such as ethylene glycol and water, propylene glycol and water, alcohol and water, or a similar mixture. Such a mixture will freeze at a temperature which depends upon the freezing points of the two individual components and their relative concentration, and remain liquid at temperatures up to about 100° F. For example, water freezes at zero degrees C., while methyl alcohol freezes at a temperature of about minus 115 degrees C. A mixture of 78% methyl alcohol and 22% water would freeze at about minus 84 degrees C. Varying percentages of the components would change the freezing point of the mixture, therefore a phase change material could be custom designed for a given material to be shipped.

Such a phase change material, if chilled to a point below its freezing temperature and then exposed to a heat source, would increase in temperature in an inverse logarithmic manner until it reached the temperature at which freezing and thawing occur for the given material, then remain at that temperature until the material is completely melted. Advantage could be thus taken of both the sensible heat and the latent heat of the phase change process.

FIG. 1 illustrates graphically the time vs. temperature behavior of heat sinks both with and without a phase change. At point 8, the initial temperature to which the heat sink is cooled before putting it into the cryogenically insulated vessel, the temperature differential between the heat sink and its environment is at a maximum. The rate of heat transfer into the heat sink is thus also at a maximum. The rate of heat transfer into the heat sink slows as a logarithmic function of time until point 10 is reached, at which temperature the phase change temperature of the phase changing heat sink material is attained. After reaching this temperature, a heat sink material which does not change phase, which material behavior is indicated by a dotted line 12 in FIG. 1, continues to heat up in the previously mentioned logarithmic manner, until it reaches the ambient temperature at time 14. However, the material which does change phase at the temperature indicated by point 10 attains a "temperature plateau", at which temperature plateau it remains relatively constant until the phase change is completed. The behavior of this phase change substance is indicated by solid line 16 in FIG. 1. Upon completion of the phase change at point 18 the phase change heat sink material resumes the logarithmic time/temperature behavior which characterized its earlier warming before the phase change incipiation, continuing to heat up until it reaches the ambient temperature at time 20. The difference between time 20 and time 14 indicates the net gain in permissible storage time due to the effect of the phase change.

In the preferred embodiment of the current invention, it is advantageous for two reasons to have as high a percentage of water in the phase change material as possible consistent with the required storage temperature of the subject biological material. The first reason is that the rate of heat gain into the container is a linear function of temperature, and a higher proportion of water in the mixture causes a higher phase change temperature, thus leading to increased allowable storage times. Secondly, water has a much higher specific heat than most other substances, thus a higher water proportion directly causes a higher thermal absorption capacity.

The rate of heat transfer into the heat sink system is always a function of the net temperature differential between the surroundings and the temperature of the system. Thus if the phase change is allowed to occur at a lower temperature than necessary for preservation of the biological materials which are to be protected, the net storage time available is decreased. This behavior is indicated by the dotted and dashed line indicated as 23 showing a phase change beginning at point 22 in FIG. 1. The net time between the beginning of the phase change at point 22 and completion of the phase change at point 24 is less than the time beginning at point 10 and ending at point 18 of the higher temperature phase change indicated by solid line 16, due to the fact that the heat transfer is occurring at a higher temporal rate. Thus the use of a lower than necessary phase change temperature material lowers the available storage time. For this reason it is a desirable point of the preferred embodiment of this invention to employ a heat sink material which changes phase at a temperature as close as possible to but still below the maximum permissible temperature of storage for the given contents. For example the previously cited mixture containing 75% methyl glycol and 25% water by weight would be correct for storing or shipping human or bovine semen at about minus 78 degrees C. while a mixture comprising about 55% ethylene glycol and 45% water would be correct for shipping or storing human blood, which has a maximum safe storage temperature of about minus 40 degrees C.

As a numerical example of the above logic, consider a typical field model liquid nitrogen storage vessel of the sort sold by Minnesota Valley Engineering. It has an advertised capacity of 17 liters (0.60 cubic feet) and a net storage time of fifty days. The latent heat of vaporization of liquid nitrogen (the amount of heat gained as it changes from a liquid to a solid) is 4294 BTU per cubic foot. Thus the 17 liters has a net thermal capacity which can be calculated as about 2579 BTU. If the 17 liters lasts 50 days at a temperature of $-329$ degrees F. while the external environment is 100 degrees F., the net rate of heat transfer into the vessel is about 0.1228 BTU per day per degree F. If we took an identical container and filled it with 17 liters of a frozen mixture of 25% water and 75% ethylene glycol, and the water-/ethylene glycol mixture had a specific heat value of about 0.562 BTU per pound per degree F. and a density of around 60 pounds per cubic foot, in heating up from an initial temperature of $-320$ degrees F. to the melting temperature of the ethylene glycol and water mixture at approximately $-109$ degrees F. the mixture would absorb approximately $(0.562)(60)(0.60)=20.2$ BTU per degree F. The time/temperature behavior of the mixture can be calculated by the equation $$\frac{T - T_\infty}{T_i - T_\infty} = e^{-\frac{.1228}{20.2} t}$$

where T = the temperature of the mixture at any given time t ,
$T_\infty$ = the ambient temperature of the surroundings, and
$T_i$ = the initial temperature of the frozen ethylene glycol and water mixture. Thus the time for the mixture to heat up from an initial temperature of $-320$ degrees F. to $-109$ degrees F. is given by:

$$t = \frac{20.2}{.1228} \times \left( -\ln \frac{-209}{-420} \right)$$

or 114 days. Given a latent heat of fusion for the ethylene glycol and water mixture of approximately 65 BTU per pound, the net latent heat available is (65) (0.600) (60)=2340 BTU, and at a heat flow rate of 0.1228 BTU per degree F. and a melting temperature of −109 degrees F., the mixture would last 96 more days before being finally melted, for a total storage time of about 210 days, vs. the 50 days storage time of the conventional liquid nitrogen tank. In a similar manner it could be shown that a total of four liters of the ethylene glycol and water mixture in a similarly designed container would equal the storage time of the 17 liter liquid nitrogen container.

It should be noted that the ethylene glycol and water mixture is not the only possible mixture which has the desired properties, but is merely an illustrative example. A mixture of ethyl alcohol and water possesses almost the same behavior as does the ethylene glycol and water mixture. An ideal substance to use as a heat sink having a phase change would possess the desired qualities of being chemically inert, nonflammable, harmless to humans animals and the environment, and inexpensive. Other substances which come near to ideal behavior include methyl alcohol and glycerine, for example.

EMBODIMENT USING SEPARATE HEAT SINK BARS

In order to deploy the system, the biological material is chilled or frozen and stored in the conventional normal manner for the given material. It is next packaged in such a manner as to allow it to be safely immersed in liquefied gas in a Dewar flask as previously discussed, or otherwise chilled. In the case of semen or embryos it is packaged in straws in such a manner as to allow it to be immersed in liquid nitrogen, or in a similar manner consistent with safe cryogenic shipment and storage. The heat sink bars discussed above may be prepared by immersing them in liquefied gas until they reach thermal equilibrium with the liquid. (At about minus 196 degrees C., in the case of nitrogen). The cryogenically insulated vessel, which has interior dimensions selected so as to conform to the desired biological material shipment plus the number of the heat sink bars needed, is next loaded with the proper number of such bars.

Alternatively, such heat sink bars might be loaded either permanently or removably in the cryogenically insulated vessel and cooled while in place. Such cooling might be accomplished by pouring a liquefied gas or other cold medium directly into the cryogenically insulated vessel or by inserting a heat exchanger attached to an external refrigeration device.

After the heat sink bars are chilled to the desired temperature, the biological material shipment is next loaded into the insulated container in such a manner that the heat sink material is between the biological material shipment and the insulated container. A cap or other end cover is then screwed or otherwise attached to the insulated container so as to hermetically seal the container.

Figure 2:
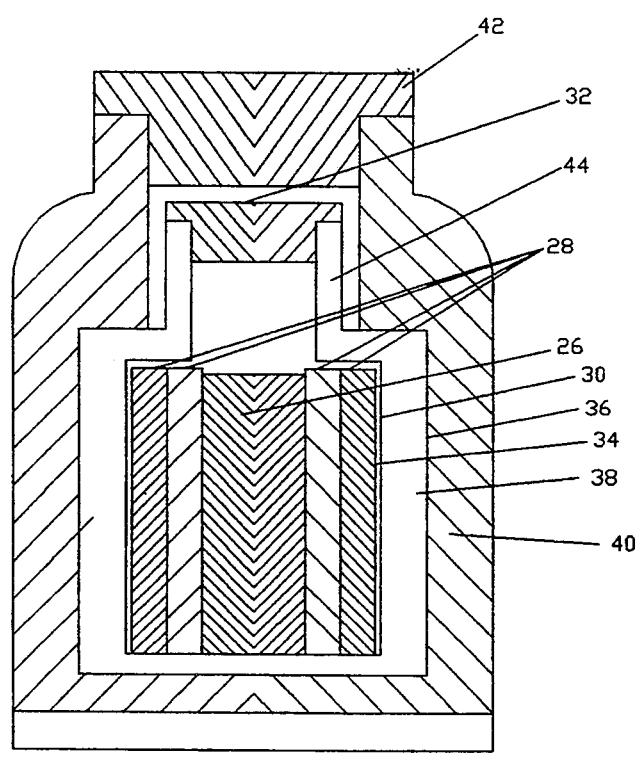
FIG. 2 shows a cross section through the side of the current invention with the use of heat sink bars which are cooled and then placed in the reusable and resealable cryogenically insulated vessel.

FIG. 2 shows a biological shipment 26 which is surrounded by a multiplicity of bars 28 which bars are composed of a heat sink material. These bars 28 are inserted together with the biological shipment 26 into cryogenically insulated vessel 30. Cryogenically insulated vessel 30 is then sealed by a tightly fitting closure 32, which is fitted into extended neck 44, which extended neck is used to minimize conduction heat gains through the neck. The space between inner wall 34 of cryogenically insulated vessel 30 and outer wall 36 of the cryogenically insulated vessel 30 is either evacuated to a strong vacuum or alternatively filled with a composite superinsulator or an evacuated powder insulator such as those insulation materials described in *Marks Standard Handbook for Mechanical Engineers*, Ninth Edition, p. 19-35, edited by Eugene A. Avallone and Theodore Baumeister, III, McGraw-Hill Book Company (1958). In the preferred embodiment the cryogenically insulated vessel 30 is contained within an outer shipping vessel 38, and the space between inner cryogenically insulated vessel 30 and outer shipping vessel 38 is filled with a secondary insulating material 40. The secondary insulating material 40 is for the purpose of protecting cryogenically insulated vessel 30 from mechanical damage as well as providing extra thermal insulation. The outer shipping vessel 38 is then sealed with a closure 42.

In the embodiment illustrated in FIG. 2 the heat sink bars 26 may be chilled by immersing them in a suitable cooling agent such as liquid nitrogen or in a mechanical refrigerator or by other cooling means before inserting them into the cryogenically insulated vessel 30. Alternatively, they might be cooled while within cryogenically insulated vessel 30 by pouring liquid nitrogen or any other liquified gas into neck 44 of vessel 30.

Figure 3:
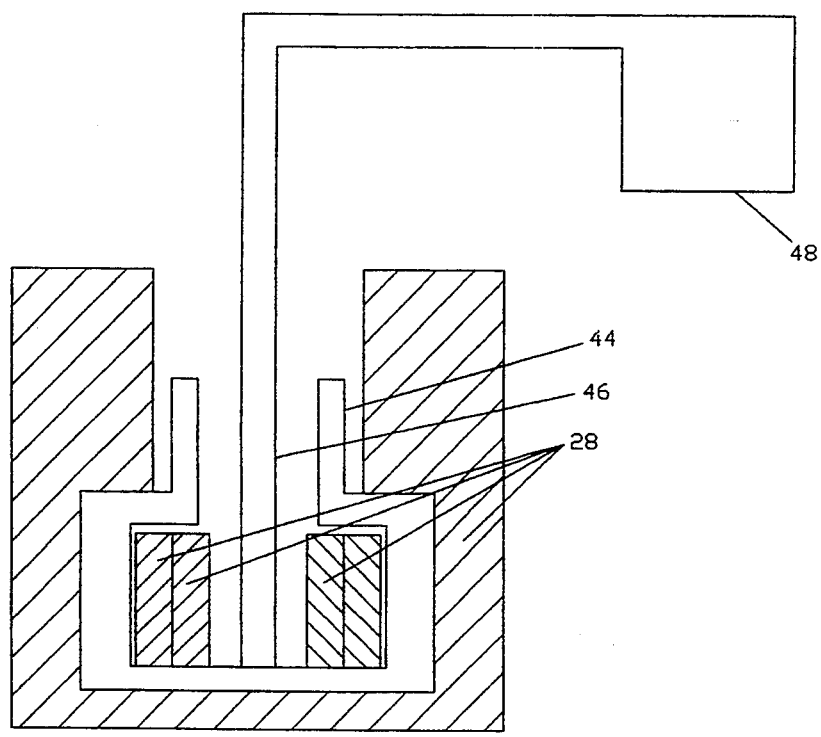
FIG. 3 shows the configuration of FIG. 2 with a heat exchange means inserted into the cryogenically insulated vessel to chill the heat sink bars before the biological materials are loaded.

As an alternate embodiment these heat sink bars 28 might be chilled by inserting a heat exchange means 46 into extended neck 44 of cryogenically insulated vessel 30, as shown in FIG. 3. The heat exchange means 46 is connected to an external refrigeration means 48, also shown in FIG. 3.

EMBODIMENT USING A SINGLE HEAT SINK MASS

If the heat sink is designed so as to be contained within the insulated outer shell rather than being formed as separate bars, the system may be cooled by pouring or injecting a liquefied gas directly into the container, or it may be cooled by means of a heat exchanger which is inserted directly into the container, which heat exchanger is connected to a separate external refrigerator.

Figure 4:
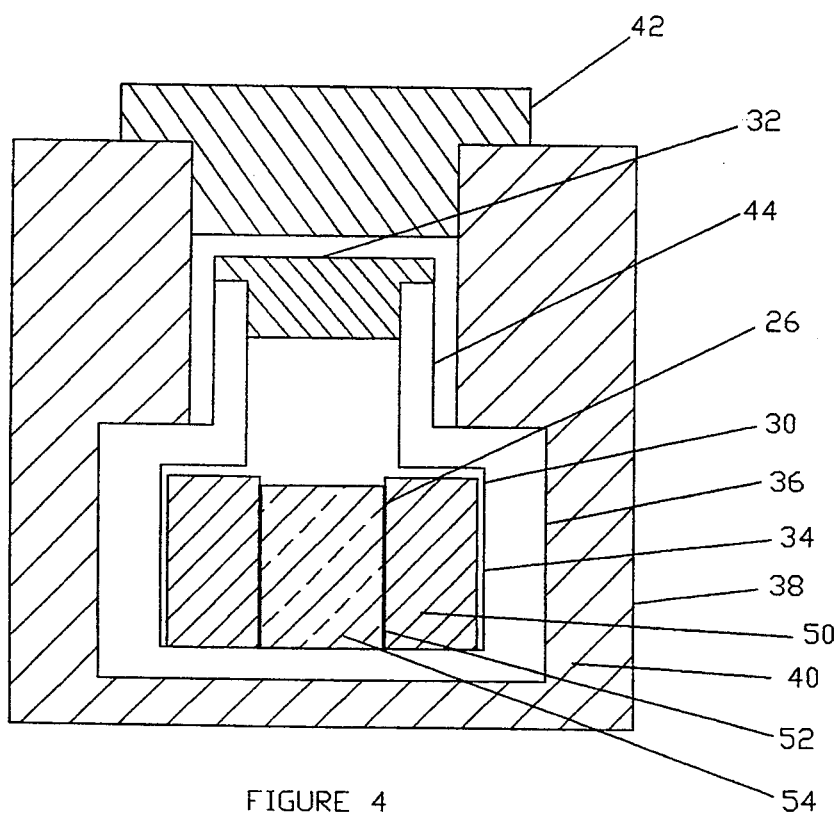
FIG. 4 shows a cross section through the side of the current invention with a heat sink designed to be contained within and cooled within the reusable and resealable cryogenically insulated vessel.

FIG. 4 shows a biological shipment 26 which is surrounded by heat sink material 50 which is permanently contained within cryogenically insulated vessel 30, which cryogenically insulated vessel 30 which is then sealed by a tightly fitting closure 32 into extended neck 44. In this embodiment of the invention the heat sink material 50 is separated from the inner space for biological shipment 26 by means of a thermally conductive mechanical separator sleeve 52, which separator sleeve is inserted into cryogenically insulated vessel 30 before the heat sink material 50 is chilled. The separator sleeve 52 serves to provide a hollow space 54 in which the biological materials are to be placed.

The space between inner wall 34 of cryogenically insulated vessel 30 and outer wall 36 of the cryogenically insulated vessel 30 is either evacuated to a strong vacuum or alternatively filled with a composite superinsulator or an evacuated powder insulator such as those insulation materials described in the previously cited *Marks Standard Handbook for Mechanical Engineers*. In the preferred embodiment the cryogenically insulated vessel 30 is contained within an outer shipping vessel 38, and the space between inner cryogenically insulated vessel 30 and outer shipping vessel 38 is filled with a secondary insulating material 40. The secondary insulating material 40 is for the purpose of protecting cryogenically insulated vessel 30 from mechanical damage as well as providing extra thermal insulation. The outer shipping vessel 38 is then sealed with a closure 42.

Figure 5:
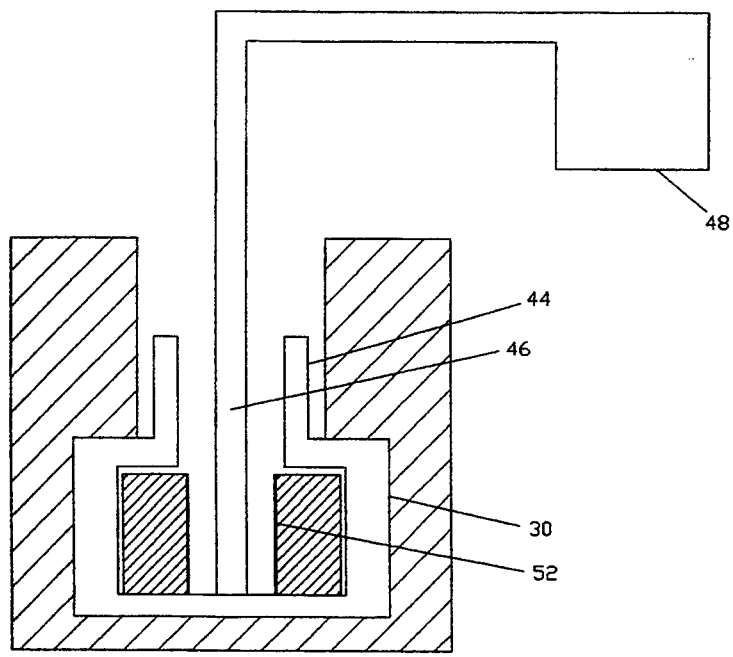
FIG. 5 shows the configuration of FIG. 4 with a heat exchange means inserted into the cryogenically insulated vessel to chill the heat sink material before the biological materials are loaded.

In the embodiment illustrated in FIG. 4 the heat sink material 50 is cooled while within cryogenically insulated vessel 30 by pouring liquid nitrogen or any other liquified gas into neck 44 of vessel 30. As an alternate embodiment this heat sink material 50 might be chilled by inserting a heat exchange means 46 into neck opening 44 and into separator sleeve 52 of cryogenically insulated vessel 30 as shown in FIG. 5. The heat exchange means 46 is connected to an external refrigeration means 48, also shown in FIG. 6.

This means of thermal protection insures that the entire internal environment of the cryogenically insulated vessel 30 is kept at an essentially isothermal state. As heat is slowly gained through the insulated container 30, it must act to heat the heat sink medium 28 or 50 to the same degree that the biological materials 26 are heated. Since the amount of heat gained through the insulation shell is a function only of the difference between the inner and outer temperatures, and is independent of the thermal capacity of the mass contained within, the prechilled heat sink(s) act as a very large thermal "buffer", permitting shipment of frozen or chilled materials in a safe and convenient manner and at a safe preservation temperature.

CONCLUSIONS, RAMIFICATIONS, AND SCOPE OF INVENTION

The reader can see that the equipment and method of the cryogenic shipping and storage system for biological materials of this invention provides a significant improvement over all prior art systems intended for the same of a similar purpose. While the above description contains many specific details, these details should not be construed as limitations on the scope of the invention, but rather as exemplifications of preferred or potential embodiments thereof. For example, many materials other than those discussed might be used for the heat sink material. Many different materials and methods of construction are conceivable for the cryogenically insulated vessel, such as commercially available thermos flasks. The commercially available Dewar shipping flask which has absorbent walls for liquid nitrogen shipment could readily adapted to soak up a mixture suitable as a heat sink material which could be frozen in place. The system could also be used for the shipment or storage of materials other than biological materials, such as foodstuffs or electronic components.

Therefore the scope of this invention should be determined by the appended claims and their legal equivalents, rather than by the specific examples given.

I claim:

1. An shipping and storage apparatus consisting of (a) a vessel insulated with a material selected from the group consisting of superinsulation materials, evacuated thin film insulation materials, and evacuated powder insulation materials, and (b) a heat sink material which is initially in the solid phase and at a temperature at least 100° F. below the temperature at which it will melt, which heat sink material is selected so as to melt at a selected temperature at least 50° F. below the freezing temperature of water, and which said heat sink material remains in the liquid state up to at least 100° F.

2. An apparatus as claimed in claim 1 wherein the heat sink material is selected from the group consisting of alcohols, glycols, benzenes, and hydrocarbons.

3. An apparatus as claimed in claim 1 wherein the heat sink material is a mixture of substances selected from the group consisting of alcohols, glycols, benzenes, hydrocarbons, and water.

4. An apparatus as claimed in claim 1, wherein said heat sink material is chilled to a temperature below its phase change temperature by a separate refrigeration means before being placed in said insulated vessel.

5. An apparatus as claimed in claim 1, wherein said heat sink material is contained permanently inside said insulated vessel and is chilled by external means such as by injecting a liquified gas into said insulated vessel.

6. An apparatus as claimed in claim 1, wherein said heat sink material is contained inside said insulated vessel in such a manner that it is removable, and wherein said heat sink material is chilled by an external refrigeration means such as by injecting a liquified gas into said insulated vessel.

7. An apparatus as claimed in claim 1, wherein said heat sink material is contained permanently inside said insulated vessel and chilled by inserting a heat exchange means into said vessel and said heat sink medium, said heat exchange means being connected to an external refrigeration means.

8. A method of shipping a frozen or chilled material, said material being contained in a reusable and resealable cryogenically insulated vessel together with a heat sink material which heat sink material is in a solid state and initially at a temperature below the temperature at which it will melt when loaded, and wherein which said heat sink material is allowed to increase in temperature during the shipping and/or storage time due to inefficiencies in said insulated vessel until it reaches its phase change temperature, at which time it remains at a fixed temperature for an extended time span, and in which said heat sink material is selected so as to have a phase change temperature at least 2° C. below the maximum permissible storage temperature of said frozen or chilled material, and in which said heat sink material is composed of a substance which will remain in a liquid state at a temperature of up to at least 100° F.

9. A method as claimed in claim 8, wherein said heat sink material is chilled to a temperature below its phase change temperature by a separate refrigeration means before being placed in said cryogenically insulated vessel.

10. A method as claimed in claim 8, wherein said heat sink material is contained permanently inside said cryogenically insulated vessel and is chilled by external refrigeration means by injecting a liquified gas into said cryogenically insulated vessel.

11. A method as claimed in claim 8, wherein said heat sink material is contained inside said cryogenically insulated vessel in such a manner that it is removable, and wherein said heat sink material is chilled by an external refrigeration means by injecting a liquified gas into said insulated vessel.

12. A method as claimed in claim 8, wherein said heat sink material is contained permanently inside said insulated vessel and chilled by inserting a heat exchange means into said vessel and said heat sink material, said heat exchange means being connected to an external refrigeration means.

13. An apparatus consisting of a reusable and resealable cryogenically insulated vessel containing a heat sink material which heat sink material is the solid state and initially at a temperature below the temperature at which it will melt when the vessel is loaded, and which heat sink material will remain in the liquid state up to a temperature of at least 100° F., and which heat sink material is allowed to increase in temperature during the shipping and/or storage time due to inefficiencies in said insulated vessel until it reaches its phase change temperature, at which temperature it remains at a fixed temperature for an extended time span, and in which said phase change material is selected so as to have a phase change temperature at least 2° F. below the maximum permissible storage temperature of said frozen or chilled material, said cryogenically insulated vessel being insulated by a material selected from the group consisting of superinsulation materials, evacuated thin film insulation materials, or evacuated powder insulation materials.

14. An apparatus as claimed in claim 13, wherein said heat sink material is chilled to a temperature below its phase change temperature by a separate refrigeration means before being placed in said cryogenically insulated vessel.

15. An apparatus as claimed in claim 13, wherein said heat sink material is contained permanently inside said cryogenically insulated vessel and is chilled by external means by injecting a liquified gas into said cryogenically insulated vessel.

16. An apparatus as claimed in claim 13, wherein said heat sink material is contained inside said cryogenically insulated vessel in such a manner that it is removable, and wherein said heat sink material is chilled by an external refrigeration means by injecting a liquified gas into said insulated vessel.

17. An apparatus as claimed in claim 13, wherein said heat sink material is contained permanently inside said insulated vessel and chilled by inserting a heat exchange means into said vessel and said heat sink material, said heat exchange means being connected to an external refrigeration means.

* * * * *